United States Patent
Rettig et al.

(10) Patent No.: US 6,678,045 B2
(45) Date of Patent: Jan. 13, 2004

(54) DEVICE FOR OPTICAL MEASUREMENT IN A MEDIUM

(75) Inventors: Ulrich Rettig, Wielenbach (DE); Rudolf Schuhmacher, Peissenberg (DE); Raimund Essel, Weilheim (DE); Markus Probst, Peissenberg (DE); Andreas Mues, Melsdorf (DE)

(73) Assignee: WTW Wissenschaftlich-Technische Werkstaeten GmbH & Co. KG, Weilheim (DE)

( * ) Notice: Subject to any disclaimer, the term of this patent is extended or adjusted under 35 U.S.C. 154(b) by 0 days.

(21) Appl. No.: 10/140,450

(22) Filed: May 6, 2002

(65) Prior Publication Data

US 2002/0167664 A1 Nov. 14, 2002

(30) Foreign Application Priority Data

May 11, 2001 (EP) .............................. 01111522

(51) Int. Cl.$^7$ .............................................. G01N 21/00
(52) U.S. Cl. ...................................................... 356/338
(58) Field of Search ............................... 356/337–343; 250/574, 575

(56) References Cited

U.S. PATENT DOCUMENTS 5,679,581 A * 10/1997 Miyazaki et al. ........... 436/517
6,281,973 B1 * 8/2001 Trainer ....................... 356/342

* cited by examiner

Primary Examiner—Michael P. Stafira
(74) Attorney, Agent, or Firm—Smith-Hill and Bedell

(57) ABSTRACT

The invention relates to an optical measuring device, more particularly for measuring turbidity in a medium comprising a housing, more particularly of metal, at least one sensor arranged in the housing including at least one radiation source for beaming at least one optical beam into the medium to be investigated, and at least one detector for detecting the scattering or reflections of the beam in the medium, at least one optically transparent element in a housing wall for beam emergence/incidence from/into the housing, at least one vibrator mechanical coupled at least to the optically transparent element, wherein a) the vibrator is arranged between the sensor and the optically transparent element, and b1) the vibrator contains at least one opening or passageway for beam passage and/or b2) the beam is steered between and through parts of the vibrator(s) into/out of the housing. This achieves a compact optical measuring device for reliable measurement even in heavily polluted media.

10 Claims, 1 Drawing Sheet

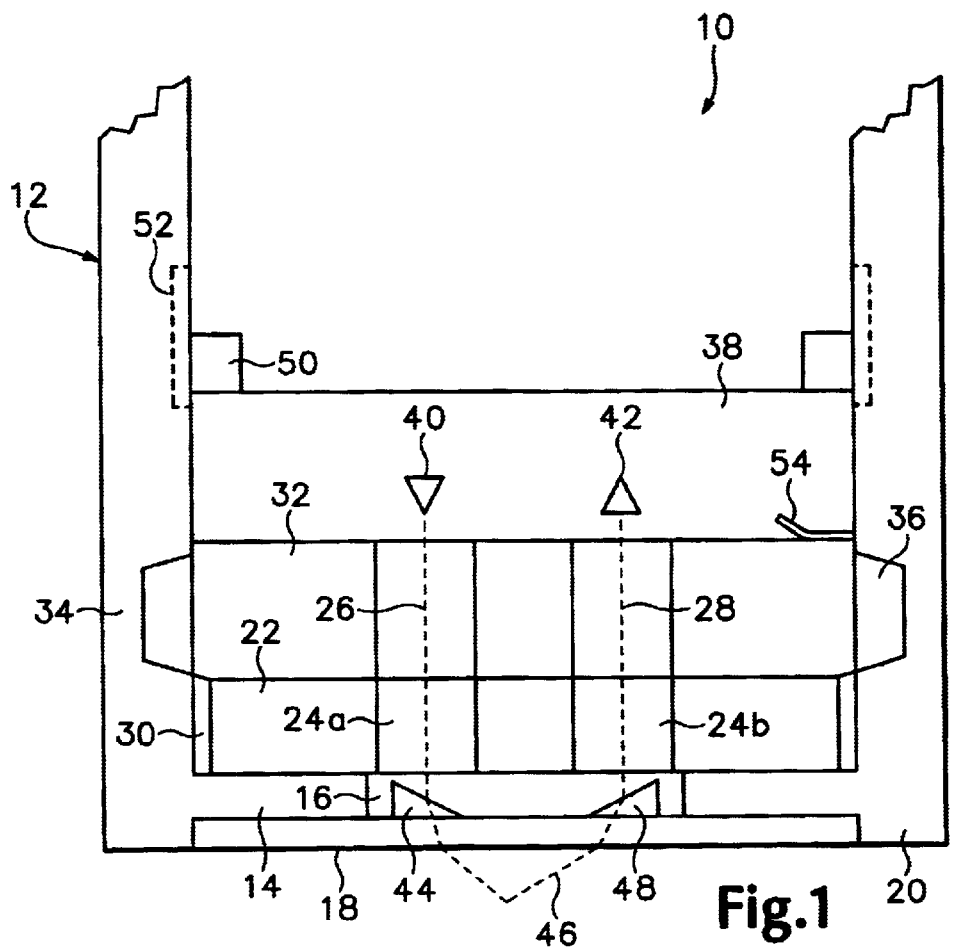
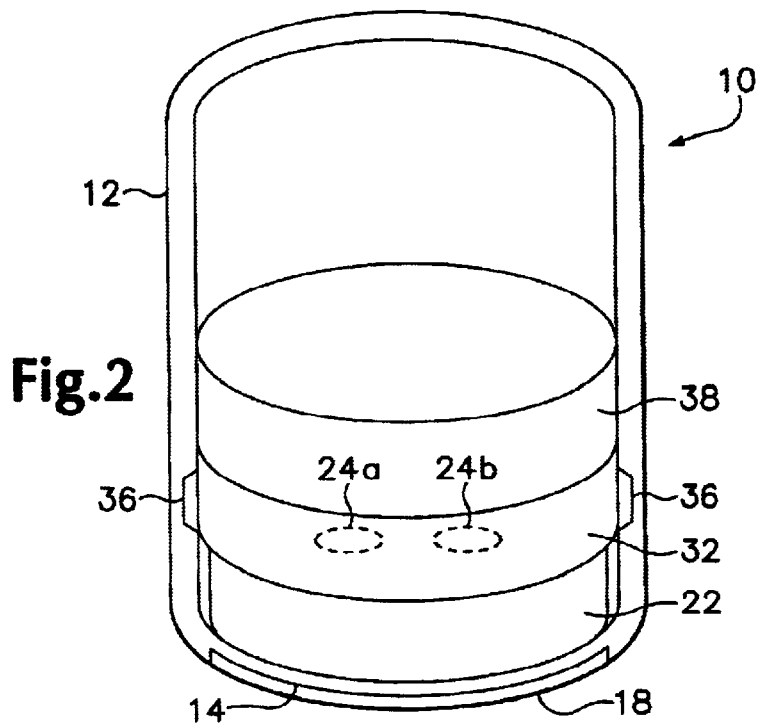

DEVICE FOR OPTICAL MEASUREMENT IN A MEDIUM

BACKGROUND OF THE INVENTION

The invention relates to a device for optical measurement, e.g. measuring turbidity, solids content and photometric sensing in media, more particularly fluids such as e.g. water and waste water. Since this very often involves measurements in heavily polluted waters there is a problem in cleaning, and maintaining clean, the measuring instruments. Dirt collecting on the measurement window detriments the measuring accuracy, it being particularly in long-term measurements that soilage of the measurement window may result in the sensed values becoming increasingly divorced from the true values. This is caused, for one thing, by biological growth, i.e. biofilms forming on the measurement window, and for another, also by such physical effects as e.g. window sedimentation and adhesion.

Known cleaning means work in making use of wipers which sweep the measurement window. This has, however, the disadvantage that the measurement window becomes smeared and dirt sticking to the wiper. In addition, it is not possible to make a measurement during cleaning which is unfavorable for long-term measurements.

Another method uses a jet of water for jetting the measurement window clean. This fails, however, to fully prevent the measurement window from becoming fouled. In addition dirt is prone to collect on protruding means such as e.g. nozzles and supporting elements. But, above all, this method introduces clean water into the medium being measured which directly influences the measurement results.

It is furthermore known in general to employ ultrasound for cleaning objects. Thus, e.g. U.S. Pat. No. 4,441,796 discloses a film transport assembly in which a lens located in the path of the optical beam is caused to vibrate in the ultrasonic range to remove dirt from the lens. However, the assembly as shown is much too bulky and ineffective to achieve good cleaning for other purposes.

It is thus the objective of the invention to provide a device of the aforementioned kind which permits non-falsified optical measurements without the measurement window becoming dirty.

This objective is achieved by a device or assembly as set forth in claim 1. Advantageous further embodiments of the invention form the subject matter of the sub-claims.

SUMMARY OF THE INVENTION

In accordance with the invention the device comprises a more particularly water-tight housing formed e.g. by a cylindrical beaker. In the region of one outer side of the housing, e.g. the face an optically transparent element, i.e. a measurement window is provided to permit directing the beam path of a sensor from/into the housing. The vibrator is arranged between the sensor and the measurement window. It contains at least one hole or opening for passage of the beam. As an alternative the vibrator may also be formed by several parts between which the incident/emerging beam of the sensor is guided.

This configuration in accordance with the invention achieves a highly compact and dense configuration of the measurement device suitable for measurement on-site. By arranging the vibrator between the sensor and the measurement window it is now possible to combine the vibrator and measurement window into a compact block without exposing the vibrator to the fluid being investigated. On the other hand, this assembly allows the sensor to be located spaced away from the measurement window and thus acoustically damped relative to the vibrator block of the vibrator and measurement window. This damping may be achieved by a reduction in the wall thickness of the housing and/or by locating damping material between the vibrator and sensor. By providing corresponding openings inline in the sealing material and vibrator it is now possible to steer the measurement beams as desired without the overall design becoming too complicated. The assembly in accordance with the invention thus permits effective mechanical coupling of a rugged vibrator, preferably a piezoceramic disk, with the measurement window whilst achieving a good mechanical decoupling of all vibrating components from the sensor. This results in an extremely reliable mode of operation permitting effective cleaning of the measurement window even during the measurement without detrimenting the measuring accuracy of the sensor. In addition to the compact design extremely highly reliable operation is assured by the assembly in accordance with the invention.

When the housing is configured to advantage as a cylindrical or beaker-shaped element, the measurement window is preferably configured as a face pane. The pane may be secured to a frame in the housing and/or to a ledge thereof to which the vibrator is then likewise coupled in a mechanical solid or rigid connection. It is, however, just as possible to fixedly connect the vibrator to the housing and to secure the measurement window to the vibrator. In any case a sealed joint between the measurement window and housing needs to be assured. The vibrator works preferably in the ultrasonic range, i.e. between 2 and 100 kHz, it preferably being arranged in a Faraday cage shielded from the sensor. The cage may be formed by the wall and ledges of the housing and/or solely by the housing walls and contact pads of the vibrator or of the sensor which are then required to extend over the full face. It is in this way that the electronics of the sensor are shielded from interference radiation which in turn adds to the resolution, reliable operation and accuracy of the measurement assembly.

Preferably, between the vibrator and the optically transparent element a housing diaphragm is configured defining both the vibrator and the optically transparent element. Securing the two components to the diaphragm of the housing is of advantage from a jointing point of view since both components require to be defined differingly by the housing. The optically transparent element, in other words the measurement window, can be positively frame-clasped by the housing and/or preferably likewise bonded full-surface to the diaphragm. Due to the consolidation of vibrator/diaphragm/measurement window a vibrator unit is now available which is easy to decouple from the remaining housing (damping reduction in water-tight housing) whilst being highly effective in preventing soilage of the measurement window and avoiding sensing and analysis being detrimented by the vibrations due to the unit being well damped from the other components.

A particularly compact design and advantageous mode of operation is achievable by arranging for the beam emerging from the housing and the scattered or reflected radiation to be at a specific angle to each other and relative to the housing; incident and emerging beam thus being at an angle in the range 10 to 120° on having left the measurement window.

The measurement assembly as described above is particularly suitable for waste water turbidity measurement in which sedimentation, i.e. the build-up of sediments and the formation of biofilms is appreciably diminished. The assembly is suitable however for all optical measurements in fluids such as e.g. water and waste water.

BRIEF DESCRIPTION OF THE DRAWINGS

The invention will now be detailed by way of an example embodiment with reference to the drawing in which:

FIG. 1 is a diagrammatic view as a vertical section through a measurement assembly in accordance with the invention and FIG. 2 is a diagrammatic view in perspective of the measurement assembly as set forth in FIG. 1 but not true-to-scale.

DETAILED DESCRIPTION

Referring now to FIG. 1 there is illustrated how the measurement assembly 10 comprises a cylindrical housing 12, at the end face of which a bottom 14 configured as a diaphragm is arranged having an opening 16 in the middle. At the end face of the housing 12 below the diaphragm 14 a measurement window 18 is arranged positively frame-clasped by the cylindrical shell 20 of the housing. This positive connection can be improved by machining grooves or the like in the frame of the measurement window 18. In addition to being positively connected to the cylindrical shell 20 the measurement window 18 may also be bonded to the diaphragm 14 as an alternative or in addition thereto. Mounted on the inner side of the housing to the diaphragm 14 is a vibrator 22 in the form of a piezoceramic disk e.g. by bonding, the piezoceramic disk comprising on the inner side two holes 24a,b for passage of an emerging beam 26 and incident radiation 28. At its end faces facing away from each other the vibrator features large pad electrodes extending more particularly over the full end face. In the circumferential portion 30 of the vibrator 22 an annular space is left open to inhibit damping of the various vibration modes by the housing. At the inner side of the housing, adjoining the vibrator 22 is a cylindrical damping lining 32 comprising beam passageways inline with the beam passageways 24a,b of the vibrator 22. In the circumferential region of the damping lining 32 and/or vibrator 22 the thickness of the housing wall 34 is reduced by a circumferential annular groove 36 being machined therein. This reduction in thickness may extend up to the end face portion of the housing, i.e. up to the portion mounting the vibrator. This results in the end face portion of the housing 12 being acoustically decoupled from the sensor 38 comprising a beam emitter 40 and a detector arranged at the inner side of the housing. The beam emerging from the beam emitter 40 can be steered through holes 24a in the damping lining 32 and vibrator 22 to a first diverter 44 which diverts the beam to the middle of the housing. The radiation 46 incident in the medium at the underside of the measurement window 18 is scattered or reflected in the medium before reentering the measurement window 18 where it enters a second diverter 48 and from there into the detector of the sensor 38. The sensor 38 is held in place by its back in a ring 50 which is screwed into the housing 12 by a female thread 52. At its side facing the damping lining 32 the sensor 38 preferably includes a pad electrode 54 which is electrically connected to the housing 12 so that the vibrator 22 is held between the pad electrode 54, housing 12 and diaphragm 14 in a kind of Faraday cage in preventing the measuring electronics of the sensor 38 being influenced by irradiation of electrical interference radiation. The housing 12 is made preferably of stainless or precious metals such as e.g. nickel chromium, chrome vanadium steels as well as aluminum, titanium, etc.

It is to be noted that the mounting fixtures and power leads on the rear side of the housing are not illustrated to make for a better overview.

What is claimed is:

1. An optical measuring device, more particularly for measuring turbidity in a medium comprising:
   a housing, more particularly of metal,
   at least one sensor arranged in said housing including at least one radiation source for beaming at least one optical beam into the medium to be investigated, and at least one detector for detecting the scattering or reflections of said beam in said medium,
   at least one optically transparent element in a housing wall for beam emergence/incidence from/into said housing,
   at least one vibrator mechanical coupled at least to said optically transparent element, wherein
   a) said vibrator is arranged between said sensor and said optically transparent element, and
   b1) said vibrator contains at least one opening or passageway for beam passage and/or
   b2) said beam is steered between and through parts of said vibrator(s) into/out of said housing.

2. The device as set forth in claim 1, comprising a beaker-shaped or cylindrical metal housing in which said optically transparent element is formed by a measurement window arranged at the end face of said beaker/cylinder.

3. The device as set forth in claim 1, wherein an electrical contact pad of said vibrator, more particularly facing away from said sensor, is electrically connected to said housing.

4. The device as set forth in claim 1, wherein said vibrator is configured as a piezoceramic disk whose outer circumference roughly corresponds to the outer circumference or inner circumference of said housing, said electric contacts of said vibrator are arranged on both sides of said disk facing away from each other and steering said beam is provided for by holes or openings in said disk.

5. The device as set forth in claim 1, wherein between said sensor and said vibrator and/or between said sensor and a portion e.g. of a diaphragm for securing said vibrator the thickness of said housing wall is reduced and/or a damping lining effective in the frequency range of said vibrator is arranged.

6. The device as set forth in claim 1, wherein said vibrator is located in a Faraday cage shielded from said sensor formed by housing walls and/or terminal electrode pads of said vibrator and/or of said sensor and/or by electrically conducting ledges in said housing.

7. The device as set forth in claim 1, wherein said optically transparent element is arranged on a diaphragm provided with holes at least in the beaming range configured in the region of an end face of said housing and fixedly mechanical coupling to said vibrator.

8. The device as set forth in claim 1, wherein a beam emerging from said housing and radiation incident in said housing merge following passing through said optically transparent element at an angle in the range 10 to 120° and in which at least one optical diverter is arranged between said optically transparent element and said sensor.

9. The device as set forth in claim 1, wherein said vibrator for generating vibrations is configured in the ultrasound range.

10. The device as set forth in claim 1, wherein said optically transparent element is disk-shaped and closes off one end face of said housing and in which the edges of said measurement window are positively frame-clasped by said housing.

* * * * *